(12) United States Patent
Casas

(10) Patent No.: US 9,495,577 B2
(45) Date of Patent: *Nov. 15, 2016

(54) NETWORK-BASED PATHOLOGY SYSTEM WITH DESKTOP SLIDE SCANNER

(71) Applicant: MikroScan Technologies, Inc., Carlsbad, CA (US)

(72) Inventor: Victor Casas, Vista, CA (US)

(73) Assignee: MIKROSCAN TECHNOLOGIES, INC., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,763

(22) Filed: Sep. 14, 2015

(65) Prior Publication Data
US 2016/0004902 A1    Jan. 7, 2016

Related U.S. Application Data

(63) Continuation of application No. 14/234,013, filed as application No. PCT/US2012/047527 on Jul. 20, 2012, now Pat. No. 9,230,153.

(60) Provisional application No. 61/509,946, filed on Jul. 20, 2011.

(51) Int. Cl.
*G06K 9/00* (2006.01)
*G06F 19/00* (2011.01)
(Continued)

(52) U.S. Cl.
CPC .......... *G06K 9/00134* (2013.01); *G02B 21/367* (2013.01); *G06F 19/321* (2013.01);
(Continued)

(58) Field of Classification Search
CPC ............... G06K 9/00134; H04N 5/23222; H04N 7/183; H04N 1/00095; H04N 2201/0082; G02B 21/367; G02B 21/16; G06F 19/321; G06F 19/3418

USPC ................................ 358/1.15, 474; 382/128
See application file for complete search history.

(56) References Cited

U.S. PATENT DOCUMENTS

| | | |
|---|---|---|
| 4,700,298 A | 10/1987 | Palcic et al. |
| 5,018,029 A | 5/1991 | Ekhoff et al. |

(Continued)

FOREIGN PATENT DOCUMENTS

| | | |
|---|---|---|
| WO | WO-9930264 A1 | 6/1999 |
| WO | WO-2008028944 A1 | 3/2008 |
| WO | WO-2013013117 A1 | 1/2013 |

OTHER PUBLICATIONS

Battmann et al. Telemedicine: Application of Telephathology-Remote miscroscopy for intraoperative diagnoses on frozen sections. Telemedicine pp. 1127-1130 (2000).

(Continued)

*Primary Examiner* — Kent Yip
(74) *Attorney, Agent, or Firm* — Wilson, Sonsini, Goodrich & Rosati

(57) ABSTRACT

A method for processing, saving and viewing a digital image of a microscope slide includes inserting a microscope slide into a digital slide scanner connected to an acquisition computer. A pre-scan formed from a plurality of image tiles uploaded to a network server while the pre-scan is being generated. The network server analyzes the image tiles in realtime to identify an area of interest. The acquisition computer generates a high magnification local scan of the area of interest. The local scan is formed from a plurality of local image tiles that are uploaded to the network server while the local scan is being generated. Each local image tile is viewable by a client computer in communication with the computer network while the plurality of local image tiles is being uploaded. A raw final image is then saved on the network server independent of the acquisition computer.

8 Claims, 3 Drawing Sheets

(51) Int. Cl.
*H04N 1/00* (2006.01)
*G02B 21/36* (2006.01)
*H04N 5/232* (2006.01)
*H04N 7/18* (2006.01)
*G02B 21/16* (2006.01)

(52) U.S. Cl.
CPC ...... *G06F19/3418* (2013.01); *H04N 1/00095* (2013.01); *H04N 5/23222* (2013.01); *H04N 7/183* (2013.01); *G02B 21/16* (2013.01); *H04N 2201/0082* (2013.01)

(56) References Cited

U.S. PATENT DOCUMENTS

| | | | |
|---|---|---|---|
| 5,216,500 A | 6/1993 | Krummey et al. | |
| 5,216,596 A | 6/1993 | Weinstein | |
| 5,297,034 A | 3/1994 | Weinstein | |
| 6,101,265 A | 8/2000 | Bacus et al. | |
| 6,208,374 B1 | 3/2001 | Clinch | |
| 6,272,235 B1 | 8/2001 | Bacus et al. | |
| 6,452,625 B1 | 9/2002 | Kapitza | |
| 6,606,413 B1 | 8/2003 | Zeineh | |
| 6,674,881 B2 | 1/2004 | Bacus et al. | |
| 6,711,283 B1 | 3/2004 | Soenksen | |
| 6,905,300 B1 | 6/2005 | Russum | |
| 7,028,075 B2 | 4/2006 | Morris | |
| 7,035,478 B2 | 4/2006 | Crandall et al. | |
| 7,116,437 B2 | 10/2006 | Weinstein et al. | |
| 7,116,440 B2 | 10/2006 | Eichhorn et al. | |
| 7,149,332 B2 | 12/2006 | Bacus et al. | |
| 7,215,467 B2 | 5/2007 | Nakagawa | |
| 7,224,839 B2 | 5/2007 | Zeineh | |
| 7,257,268 B2 | 8/2007 | Eichhorn et al. | |
| 7,292,251 B1 | 11/2007 | Gu et al. | |
| 7,319,540 B2 | 1/2008 | Tipirneni | |
| 7,391,894 B2 | 6/2008 | Zeineh | |
| 7,432,486 B2 | 10/2008 | Tanemura et al. | |
| 7,502,519 B2 | 3/2009 | Eichhorn et al. | |
| 7,518,652 B2 | 4/2009 | Olson et al. | |
| 7,542,596 B2 | 6/2009 | Bacus et al. | |
| 7,602,524 B2 | 10/2009 | Eichhorn et al. | |
| 7,646,495 B2 | 1/2010 | Olson et al. | |
| 7,668,362 B2 | 2/2010 | Olson et al. | |
| 7,738,688 B2 | 6/2010 | Eichhorn et al. | |
| 7,755,841 B2 | 7/2010 | Christenson et al. | |
| 7,801,352 B2 | 9/2010 | Uchiyama et al. | |
| 7,826,649 B2 | 11/2010 | Crandall et al. | |
| 7,844,125 B2 | 11/2010 | Eichhorn et al. | |
| 7,856,131 B2 | 12/2010 | Bacus et al. | |
| 7,893,988 B2 | 2/2011 | Olson et al. | |
| 7,916,916 B2 | 3/2011 | Zeineh | |
| 7,941,275 B2 | 5/2011 | Gholap et al. | |
| 7,949,168 B2 | 5/2011 | Crandall et al. | |
| 7,979,212 B2 | 7/2011 | Gholap et al. | |
| 8,010,555 B2 | 8/2011 | Eichhorn | |
| 8,023,714 B2 | 9/2011 | Soenksen | |
| 8,086,077 B2 | 12/2011 | Eichhorn | |
| 8,094,902 B2 | 1/2012 | Crandall et al. | |
| 8,103,082 B2 | 1/2012 | Olson et al. | |
| 8,189,897 B2 | 5/2012 | Leidenbach | |
| 8,325,150 B1 | 12/2012 | Reeves et al. | |
| 8,456,522 B2 | 6/2013 | Olson et al. | |
| 8,515,683 B2 | 8/2013 | Gholap et al. | |
| 8,781,261 B2 | 7/2014 | Eichhorn | |
| 8,805,791 B2 | 8/2014 | Eichhorn | |
| 8,996,570 B2 | 3/2015 | Stratman et al. | |
| 2002/0061127 A1 | 5/2002 | Bacus et al. | |
| 2003/0123717 A1* | 7/2003 | Bacus | G01N 15/1475 382/128 |
| 2006/0104499 A1 | 5/2006 | Zahniser et al. | |
| 2006/0159367 A1* | 7/2006 | Zeineh | G02B 21/365 382/276 |
| 2007/0103739 A1* | 5/2007 | Anderson, Jr. | G03B 21/118 358/479 |
| 2009/0028414 A1 | 1/2009 | Crandall et al. | |
| 2009/0238435 A1 | 9/2009 | Shields | |
| 2010/0194681 A1 | 8/2010 | Halushka | |
| 2010/0315502 A1* | 12/2010 | Tafas | G02B 21/365 348/79 |
| 2011/0217238 A1 | 9/2011 | Borrebaeck et al. | |
| 2011/0311123 A1 | 12/2011 | Gholap et al. | |
| 2012/0011151 A1 | 1/2012 | Eichhorn | |
| 2012/0072452 A1 | 3/2012 | Stratman et al. | |
| 2012/0099769 A1 | 4/2012 | Eichhorn | |
| 2013/0182922 A1 | 7/2013 | Kil | |
| 2014/0193839 A1 | 7/2014 | Cunningham | |
| 2014/0333959 A1 | 11/2014 | Casas | |

OTHER PUBLICATIONS

Co-pending U.S. Appl. No. 14/848,235, filed Sep. 8, 2015.
Co-pending U.S. Appl. No. 14/925,905, filed Oct. 28, 2015.
PCT/US2012/047527 International Preliminary Report on Patentability dated Jan. 21, 2014.
PCT/US2012/047527 International Search Report dated Oct. 1, 2012.
U.S. Appl. No. 14/234,013 office Action dated Jan. 30, 2015.
U.S. Appl. No. 14/848,235 Office Action dated Oct. 29, 2015.
PCT/US2015/057890 International Search Report and Written Opinion dated Feb. 5, 2016.
Parvin et al. DeepView: A Channel for Distributed Microscopy and Informatics. Supercomputing, ACM/IEEE 1999 Conference (Nov. 13-18, 1999).
U.S. Appl. No. 14/848,235 Office Action dated Aug. 9, 2016.

* cited by examiner

NETWORK-BASED PATHOLOGY SYSTEM WITH DESKTOP SLIDE SCANNER

CROSS-REFERENCE

This application is a continuation of Ser. No. 14/234,013, filed May 19, 2014, which is a U.S. National Phase of PCT/US2012/047527, filed Jul. 20, 2012, which claims the benefit of U.S. Provisional Application No. 61/509,946, filed Jul. 20, 2011, all of which are incorporated herein by reference in its entirety.

FIELD

The following description relates generally to slide scanners, and in particular to desktop slide scanners for network-based pathology.

BACKGROUND

In order to diagnose a disease it is often necessary to examine tissue samples at high magnification. By locating and identifying anomalous features in a tissue sample, a pathologist can make a diagnosis, help the patient's physician select appropriate treatment and provide information on the efficacy of previous treatments. Pathologists are therefore critical to the diagnosis and treatment of many diseases.

In general, pathologists often work at locations geographically distant from the hospital or clinic at which a tissue sample is taken. In the past it was necessary to physically transport a tissue sample from the location of the patient to the pathologist, for example by express mail or courier. A pathologist would then prepare a slide specimen from the tissue sample and examine it under a microscope. However, physically transporting the tissue sample to the pathology laboratory may be time consuming, particularly if the patient is in a rural or remote area. Furthermore, if the tissue sample crosses a border, it must be inspected by customs officials. Finally, in many areas such as third world countries there simply are not many pathologists, thereby making it necessary for pathologists to spend an inordinate amount of time travelling to different facilities. For patients who require immediate diagnosis, this is a serious drawback.

The advent of digital pathology helped to alleviate this problem. In digital pathology, a high resolution digital scan of a slide is taken and this image is electronically transmitted to the pathologist for analysis. A physician or technician can prepare slides from tissue samples and create high resolution scans for off-site analysis by the pathologist. Furthermore, high volume slide scanners may scan dozens of slides per scanning operation. Thus, dozens of different slide specimens from one or more nearby medical facilities may be sent to a single location with a high volume slide scanner where digital images or "virtual slides" are created. These virtual slides are then electronically transmitted to appropriate pathologists over a computer network such as the internet.

Thus, digital pathology and high volume slide scanners have helped streamline pathological analysis by creating a hub to which all physical slides in a region may be sent. The high volume scanner at the hub is then used to electronically distribute virtual slides to pathologists anywhere in the world almost instantly. In other words, it is no longer necessary to send individual slides to pathologists in a number of specialized fields. Instead, all slides may be sent to the location of the high volume slide scanner, which is typically relatively near the medical facility where the tissue sample was taken compared to the location of the appropriate pathologist However, although digital pathology with high volume slide scanners is an improvement over older pathology methods, it is not without drawbacks. First, existing high volume slide scanners are very large and expensive, often costing several hundred thousand dollars. This cost may be prohibitive, particularly in less wealthy countries and/or rural areas. Additionally, high volume scanners are generally loaded with slides only once a day. If an anomaly is found in a particular slide, it cannot be immediately removed or rescanned at a higher resolution for more detailed analysis. Further, high volume scanners are typically allotted to physicians only as workload allows so a physician may have to wait one or more days before it is possible to scan a new slide.

Finally, another drawback to conventional digital pathology is that very high demands are placed on the computer acquiring the image from the scanner. The acquired images are typically several gigabytes in size, and thus a powerful computer is required to quickly process, manipulate and analyze the images. These computers are generally very expensive, making the combination of a high volume slide scanner and acquisition computer cost prohibitive for many facilities.

In summary, high volume scanners are helpful for streamlining digital pathology and handling a large number of slides at once, but there remains a need for a smaller, more affordable, more flexible and more responsive digital pathology system.

SUMMARY OF THE INVENTION

The embodiments of a desktop slide scanner for cloud-based pathology disclosed below satisfy these and other needs. The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, a method for processing, saving and viewing a digital image of a microscope slide includes providing an acquisition computer connected to a network server in communication with a computer network. At least one microscope slide is inserted into a digital slide scanner connected to the acquisition computer. The acquisition computer generates a pre-scan of the microscope slide at a pre-scan magnification and a pre-scan resolution. The pre-scan is formed from a plurality of sequentially scanned image tiles acquired by the acquisition computer. The acquisition computer uploads each of the plurality of image tiles to the network server as each image tile is scanned. The network server analyzes the image tiles while the pre-scan is being generated to identify an area of interest in the pre-scan. The acquisition computer generates a local scan of the area of interest at a second magnification higher than the pre-scan magnification. The local scan is formed from a plurality of local image tiles acquired by the acquisition computer. The acquisition computer uploads each of the plurality of local image tiles to the network server while the local scan is being generated. Each local image tile is viewable by a client computer in communication with the computer network while the plurality of local image tiles is being uploaded. The network server assembles a raw final image of the local scan from a mosaic of the plurality of local image tiles. The raw final image is then saved on the network server independent of whether the raw final image is saved on the acquisition computer.

In some embodiments, the above method may also include sharpening each local image tile to create a plurality of sharpened local image tiles while the plurality of local image tiles is being uploaded. The network server assembles a sharpened final image from the plurality of sharpened local image tiles while the plurality of local image tiles is being uploaded. The client computer has the ability to select between the raw final image and the sharpened final image for immediate viewing without saving the raw final image and/or the sharpened final image locally and without transferring the entire raw final image and/or the entire sharpened final image after the acquisition computer generates the local scan.

In other embodiments, a method for remotely analyzing a digital image of a microscope slide includes providing an acquisition computer connected to a network server in communication with a computer network. At least one microscope slide is inserted into a digital slide scanner connected to the acquisition computer. The digital slide scanner includes a microscope and a microscope stage, and a pre-scan of a microscope slide on the microscope stage is generated at a first magnification. A client computer remote from the acquisition computer and connected to the computer network is also provided. A pathologist remotely views the pre-scan on the client computer to identify areas of interest in the microscope slide. The digital slide scanner generates a live stream of the areas of interest of the pre-scan at a second magnification greater than the first magnification. The pathologist then remotely instructs the digital slide scanner to move the microscope stage to analyze different portions of the areas of interest in real time.

The pathologist may use the client computer to remotely focus the microscope on regions of varying depth in the areas of interest in real time. Additionally, the desktop slide scanner may also include an inker that marks the microscope slide in the areas of interest identified by the pathologist.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION OF THE INVENTION

Figure 1:
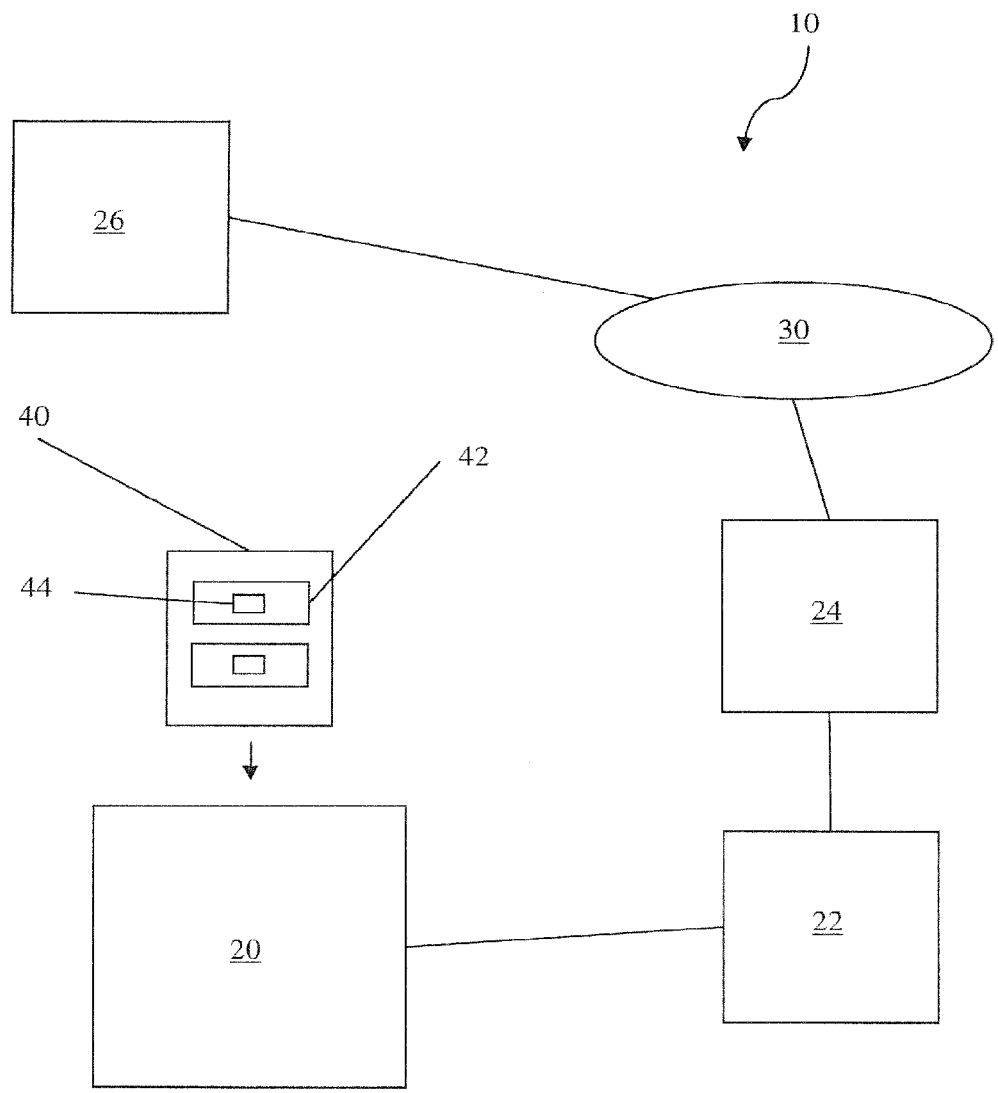
FIG. 1 is a schematic drawing showing the architecture of a network-based pathology system with desktop digital slide scanner.

In one aspect of the disclosed embodiments, a method for processing, saving and viewing a digital image of a microscope slide includes inserting a microscope slide into a digital slide scanner connected to an acquisition computer. A pre-scan formed from a plurality of image tiles uploaded to a network server while the pre-scan is being generated. The network server analyzes the image tiles in real-time to identify an area of interest. The acquisition computer generates a high magnification local scan of the area of interest. The local scan is formed from a plurality of local image tiles that are uploaded to the network server while the local scan is being generated. Each local image tile is viewable by a client computer in communication with the computer network while the plurality of local image tiles is being uploaded. A raw final image is then saved on the network server independent of whether it is saved on the acquisition computer.

The presently disclosed embodiments facilitate fast and accurate pathological analysis of tissue samples taken from a patient. A physician and/or technician obtains a tissue sample and prepares a microscope slide from the tissue sample in a conventional manner. The slide is then brought to a facility with a digital slide scanner as described below.

The digital slide scanner of the presently disclosed embodiments is much smaller than conventional high volume slide scanners, and ideally is a desktop slide scanner. Unlike high volume slide scanners, the desktop slide scanner only scans a handful of slides at a time. For example, the desktop slide scanner may include a cartridge capable of accommodating between one and ten slides depending on slide size, although cartridges capable of holding more than ten slides are also contemplated. Once the prepared slides are placed in the cartridge, the cartridge is inserted into the desktop slide scanner which can then be activated to prepare a pre-scan of the slides.

The desktop slide scanner is connected to a local acquisition computer which is connected to a network server in communication with a computer network. Throughout this disclosure, it is to be understood that any connection or communication between any two computers or devices may be physical or wireless. Once the cartridge is inserted into the desktop slide scanner, a user may instruct the desktop slide scanner to prepare a pre-scan of a slide in the cartridge. The pre-scan is at a relatively low magnification to ensure that the entire tissue sample in the slide falls within the borders of the scan area. The pre-scan is formed from a mosaic of image tiles which are sequentially uploaded to the network server as each image tile is scanned. The network server stitches together each image tile as it is received until the entire pre-scan image is formed.

It should be noted that by uploading the image tiles forming the pre-scan to the network server in real-time, it is possible to generate a complete pre-scan image without ever saving the pre-scan image locally on the acquisition computer. In other words, the acquisition computer may act as an intermediary for acquiring the image data and uploading it to the network server without ever storing, processing or analyzing the image data. The network server, on the other hand, handles all of the computationally intensive operations on the image data. This network-based structure enables conservation of computational resources by centralizing the most computationally intensive operations on the network server, thereby enabling the acquisition computer and client computer to be less powerful than would be necessary if they were required to locally store and process the image data.

As the network server receives each of the image tiles and stitches them together to form the pre-scan image, it is analyzing the image tiles in real time to automatically identify a local area of interest one the slide. By identifying areas of high contrast in the pre-scan image the network server determines the edges of the tissue sample on the slide. The network server may also be programmed to automatically identify features or anomalies within the tissue sample. Alternatively, a user of a client computer connected to the network server via a computer network may manually identify a local area of interest on the slide. The user may choose either the automatically or manually identified local area of interest for further analysis at higher magnification. Additionally, the client computer may include software for automatically identifying anomalies or other areas of interest in the tissue sample.

Once the local area of interest is identified either automatically or manually, the network server sends instructions to the acquisition computer to commence scanning the local area of interest at a higher magnification. The desktop slide scanner scans the local area of interest by sequentially scanning a mosaic of local image tiles. The acquisition computer uploads each local image tile to the network server as each local image tile is scanned. The network server stitches each local image tile together as the image tiles are being uploaded. Once all local image tiles have been uploaded and stitched together, a raw final image of the local area of interest is produced.

In some embodiments, because the local image tiles are uploaded to the network server in real-time as they are scanned, a user of a client computer connected to the network server via a computer network is able to view the local image tiles in real-time. In other words, a user of the client computer, for example a pathologist, can view the raw final image as it is stitched together piece by piece even though the local image tiles are not saved on the client computer. This enables the user to more quickly identify anomalies in the tissue sample because it is not necessary to wait until the entire raw final image is scanned before the individual local image tiles can be viewed. However, in other embodiments the local image tiles are not viewable by a user of the client computer until all local image tiles are uploaded to the network server and mapped with coordinates. In such embodiments, the lag time between beginning the upload of image tiles to the network server and viewing/analyzing the final image on the client computer may be approximately 3-5 minutes depending on image size and bandwidth.

The network server may optionally automatically sharpen each of the local image tiles as they are uploaded to form a sharpened final image. The user of the client computer is then able to view both the raw final image and the sharpened final image even though neither final image is stored locally on the client computer. By providing images that are automatically sharpened using known image processing methods, identification of anomalies in tissue samples may be facilitated in some cases.

Additionally, the client computer may be equipped with software for analyzing and annotating the images stored on the network. For example, the software may enable a user to annotate features of the image for more detailed analysis. The user may move an onscreen pointer to different areas of interest in an image of a sample and digitally mark those areas and optionally enter notes detailing why the area should be analyzed in more depth. In this way the client software allows the user to generate a list of areas of interest that can be accessed by the acquisition computer over the computer network. In some embodiments, these areas of interest may also be physically marked on the slide in the desktop scanner using a built-in ink ejector that places a small drop of ink on each identified area of interest.

When directed to do so by the user of the client computer, the acquisition computer can then direct the desktop slide scanner to automatically scan each area of interest identified in the list at a higher magnification so that the user can then analyze those areas in greater detail. By only scanning the areas of interest at a higher magnification and not scanning the entire slide at higher magnification, computational resources are conserved and the total scan time is greatly shortened. Of course, it is also possible to scan the entire slide at the higher magnification if the user of the client computer wishes to analyze the entire sample in greater detail.

A sample architecture for a network-based pathology system with desktop slide scanner will now be described with reference to FIG. 1. Pathology system 10 includes desktop slide scanner 20 connected acquisition computer 22 which is connected to network server 24. It should be noted that any connected between devices in pathology system 10 may be wired or wireless, and further that the connections between devices may comprise local networks. Network server 24 is connected to computer network 30 which, in some embodiments, may be the internet. Also connected to computer network 30 is client computer 26 which includes user interface software that allows a user of client computer 26 to upload and download data from computer network 30. For example, in some embodiments the user interface software may include a web browser with one or more extensions, plug-ins, add-ons, or other embedded software that enhances the ability of client computer 26 to interact with and/or control one or more other devices in pathology system 10.

Network server 24 may include software for analyzing, editing and modifying data received from acquisition computer 22. For example, network server 24 may include software for analyzing image data to identify areas of interest in an image and software for sharpening an image, improving image contrast or otherwise modifying an image to facilitate image analysis by a user of client computer 26. Computer network 30 may include storage devices for storing large data files uploaded to computer network 30 from network server 24. Computer network 30 may also include additional computers for processing data uploaded by network server 24 to computer network 30 in order to distribute the computational power required for data analysis and processing.

Pathology system 10 also includes slide cartridge 40 which holds one or more sample slides 42. Each sample slide 42 includes a tissue sample 44 which is placed on each slide 42 by a technician, physician or pathologist. Slide cartridge 40 is inserted into desktop slide scanner 20 which includes a microscope and digital imaging device for magnifying and digitizing images of tissue samples 44 on sample slides 42.

Figure 2:
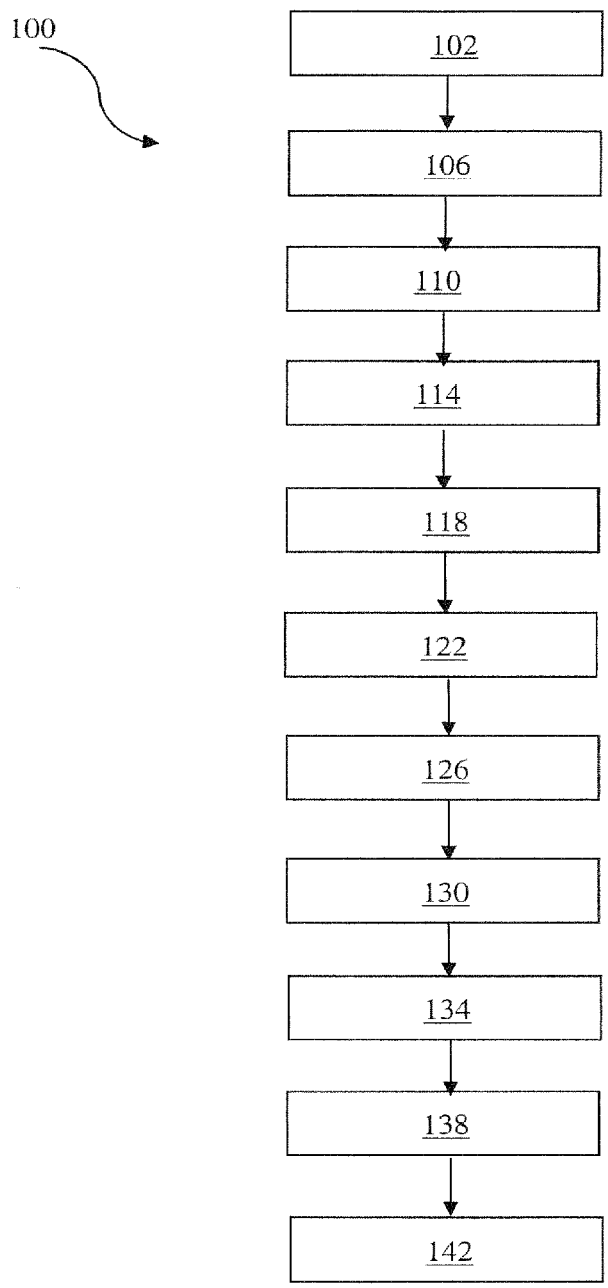
FIG. 2 is a flow chart showing the process of uploading images of a microscope slide to a network server for remote analysis.

A first method of using pathology system 10 will now be described with reference to FIG. 2. Method 100 begins by providing an acquisition computer and a client computer both in communication with a computer network (102). A desktop slide scanner in communication with the acquisition computer is also provided (106). A microscope slide with a tissue sample is inserted into the desktop slide scanner for magnification of the tissue sample and providing a digital image of the tissue sample (110). The acquisition computer directs the desktop slide scanner to scan the tissue sample on the microscope slide by dividing the viewable area of the microscope slide into a grid and sequentially scanning image tiles which when digitally stitched together form a pre-scan taken at a first magnification and first resolution (114). The image tiles are sequentially uploaded by the acquisition computer to the network server in real time as the image tiles are obtained by the acquisition computer from the desktop slide scanner (118). The network server may analyze image tiles while the pre-scan image is being generated and stitched together to identify areas of interest in the pre-scan image in real time (122).

The acquisition computer then directs the desktop slide scanner to scan identified areas of interest in the tissue sample at a second magnification higher than the first pre-scan magnification (126). Each local area of interest is divided into a grid so that the local scan of the area of interest comprises a plurality of local image tiles that are generated and uploaded to the network server sequentially (130). The network server stitches the local image tiles together as they are uploaded (134). A user of the client computer is able to view the local image tiles in real time as the raw final image of the local area of interest is being stitched together and uploaded by the network server (138). A raw final image comprising a mosaic of the assembled local image tiles is generated and saved on the network server independent of whether the raw final image is saved on the acquisition computer (142).

Figure 3:
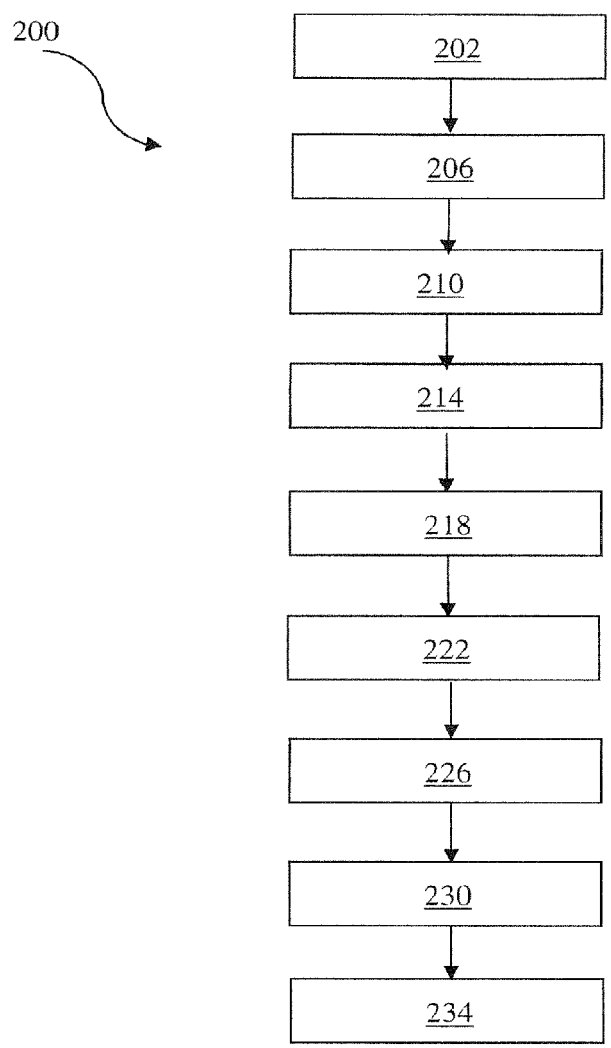
FIG. 3 is a flow chart showing the process of live streaming images of a microscope slide from a desktop digital slide scanner to a remote client.

Another method of using pathology system 10 will now be described with reference to FIG. 3. Method 200 begins by providing an acquisition computer and a client computer both in communication with a computer network (202). A desktop slide scanner having a microscope stage is placed in communication with the acquisition computer (206). A microscope slide with a tissue sample is inserted onto the stage of the desktop slide scanner for magnification of the tissue sample and providing a digital image of the tissue sample (210). A pre-scan of the tissue sample on the microscope slide is taken at a first magnification and uploaded to the network server by the acquisition computer (214). A user of the client computer remote views the pre-scan over the computer network and analyzes the pre-scan to identify areas of interest in the pre-scan (218). The desktop slide scanner moves the microscope stage to focus on the identified areas of interest at a second magnification higher than the first pre-scan magnification (222). The acquisition computer uploads a live stream of the identified areas of interest (226). The user of the client computer views the live stream in real time and remotely instructs the digital slide scanner to move the microscope stage so that different portions of the identified areas of interest can be viewed and analyzed in real time (230). The user of the client computer may also remotely instruct the desktop slide scanner to focus at different depths of the tissue sample in real time (234).

It should be noted that the phrase "in real time" as used above means that instructions from the client computer to the acquisition computer or desktop slide scanner are carried out immediately as they are made by the client computer and received by the remote device. The phrase "in real time" also means that image data uploaded to the network server by the acquisition computer is viewable on the client computer as soon as it is received. For example, the user of the client computer may instruct the microscope stage to move to different areas and the corresponding changing images are immediately viewable on the client computer. In other words, a series of different still images are not downloaded by the client computer; rather, the client computer receives a stream of image data that instantly changes as the microscope stage is moved in response to instructions sent by the user of the client computer.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for processing, saving and viewing a digital image of a sample comprising:
    providing an acquisition computer connected to a network server in communication with a computer network;
    inserting at least one sample into a digital scanner connected to the acquisition computer;
    the acquisition computer generating a first image of the sample at a first magnification and resolution;
    the acquisition computer uploading the first image to the network server;
    the network server analyzing the first image while the first image is being generated to identify an area of interest in the first image;
    the acquisition computer generating a local scan of the area of interest at a second magnification higher than the first magnification, the local scan comprising a plurality of local image tiles;
    the acquisition computer uploading each of the plurality of local image tiles to the network server while the local scan is being generated, each local image tile being viewable by a client computer in communication with the computer network in real time while the plurality of local image tiles are being uploaded;
    the network server stitching each local image tile together as the image tiles are being uploaded and assembling a raw final image of the local scan from a mosaic of the plurality of local image tiles; and
    saving the raw final image on the network server independent of whether the raw final image is saved on the acquisition computer.

2. The method of claim 1, further comprising:
    sharpening each local image tile to create a plurality of sharpened local image tiles while the plurality of local image tiles are being uploaded;
    the network server assembling a sharpened final image from the plurality of sharpened local image tiles while the plurality of local image tiles are being uploaded; and
    the client computer selecting between the raw final image and the sharpened final image for viewing immediately without saving the raw final image and the sharpened final image locally and without transferring the raw final image or the sharpened final image after the acquisition computer generates the local scan.

3. The method of claim 1, wherein the digital scanner comprises a microscope and a stage.

4. The method of claim 1, wherein the identifying the area of interest comprises analyzing the first image at a low resolution in real time to automatically identify the area of interest.

5. The method of claim 1, wherein the sample is a tissue sample.

6. The method of claim 5, wherein the tissue sample is from a patient.

7. The method of claim 1, wherein a user of the client computer views the local tile images in real time.

8. The method of claim 7, wherein the user is a pathologist.

* * * * *